United States Patent [19]

Takeda et al.

[11] Patent Number: 5,202,127

[45] Date of Patent: Apr. 13, 1993

[54] MOTH-PROOFING METHOD USING TRIOXANE AS SOLE ACTIVE

[75] Inventors: Mutsuhiko Takeda, Tokyo; Minoru Kakuda, Matsudo; Masafumi Shimpo, Kashiwa, all of Japan

[73] Assignee: Mitsubishi Gas Chemical Co., Inc., Tokyo, Japan

[21] Appl. No.: 816,544

[22] Filed: Dec. 30, 1991

Related U.S. Application Data

[63] Continuation of Ser. No. 468,945, Jan. 23, 1990, abandoned, which is a continuation of Ser. No. 116,150, Nov. 3, 1987, abandoned.

[30] Foreign Application Priority Data

| Nov. 4, 1986 | [JP] | Japan | 61-260770 |
| Apr. 28, 1987 | [JP] | Japan | 62-103226 |
| Aug. 18, 1987 | [JP] | Japan | 62-203477 |

[51] Int. Cl.$^5$ .................................. A01N 43/32
[52] U.S. Cl. .................................. 514/452; 424/408; 424/409
[58] Field of Search .............. 424/78; 514/452, 973, 514/970, 524.1; 206/819

[56] References Cited

U.S. PATENT DOCUMENTS

| 601,855 | 10/1905 | Dreyfus | 424/76.2 |
| 2,464,043 | 3/1949 | Komlet | 424/76.2 |
| 3,097,129 | 7/1963 | Laffetay et al. | 242/3 |
| 4,045,551 | 8/1977 | Ueno et al. | 424/311 |
| 4,439,415 | 3/1988 | Kennart et al. | 514/438 |
| 4,735,803 | 4/1988 | Katz et al. | 514/920 |
| 5,026,875 | 6/1991 | Takeda et al. | 549/368 |
| 5,043,351 | 8/1991 | Takeda et al. | 514/452 |
| 5,071,870 | 12/1991 | Takeda et al. | 514/452 |
| 5,094,846 | 3/1992 | Takeda et al. | 514/452 |

FOREIGN PATENT DOCUMENTS 1577690 8/1969 France.

OTHER PUBLICATIONS

The Merck Index, (Eleventh Edition, 1989), pp. 1324, 1160–1161, 170, 763 764, 959, 603, 1481, 1375.
Mutation Research, 136 (1984) 169–171, Kowalski, et al., "Absence of Mutagenicity of Trioxane and Dioxolane in Salmonella Typhimurium".
Chem. Abstracts 115(25):273472u K. Yohita.
Chem. Abstracts 105:166912A and Derwent Abstract.
Chem. Abstracts 96:1176652.

*Primary Examiner*—Thurman K. Page
*Assistant Examiner*—Peter F. Kulkoski
*Attorney, Agent, or Firm*—Sherman and Shalloway

[57] ABSTRACT

An insect-proofing agent comprising 1,3,5-trioxane as an active ingredient is disclosed. This insect-proofing agent has a high insect-proofing action and gives no irritating odor, and the insect-proofing agent is not toxic to human bodies and has a high safety. Furthermore, this insect-proofing agent causes no discoloration in metallic substance such as silver thread, gold threads and spangles used for clothing decoration. This insect-proofing agent is effectively applied in the form of a solid preparation, an aqueous solution or an organic solvent solution.

9 Claims, No Drawings

MOTH-PROOFING METHOD USING TRIOXANE AS SOLE ACTIVE

This application is a continuation of application Ser. No. 07/468,945, filed Jan. 23, 1990, now abandoned which is a continuation of application Ser. No. 07/116,150, filed Nov. 3, 1987 abandoned.

BACKGROUND OF THE INVENTION (1) Field of the Invention

The present invention relates to an insect-proofing agent and an insect-proofing method. More specifically, the present invention relates to an insect-proofing agent comprising trioxane as the active ingredient and an insect-proofing method using trioxane.

(2) Description of the Prior Art p-Dichlorobenzene, naphthalene and camphor have been used as sublimable insect-proofing agents, and these compounds are widely used as insect-proofing agents for preventing damage to articles of clothing, caused for example by a case making clothes moth a webbing clothes moth a varied carpet beetle and a black carpet beetles. Among these compounds, p-dichlorobenzene has a large insecticidal force and has an immediate effect and is therefore mainly used as the household moth-proofing agent.

The following properties are ordinarily required for moth-proofing agents. Namely, a moth-proofing effect is manifested in an application space for a long time, ordinarily for several months, no toxicity is given to human bodies and no unpleasant feeling is given. p-Dichlorobenzene is most frequently used as the moth-proofing agent satisfying these requirements tolerably, and in order to moderate the inherent irritating odor of p-dichlorobenzene, a perfume or the like is incorporated. However, recently, environmental contamination with p-dichlorobenzene is becoming a social problem. Namely, p-dichlorobenzene, as well as polychlorobiphenyl (PCB), is an aromatic chlorine compound and has an unnecessarily high stability and is hardly decomposable. Therefore, the environmental residual property is very high. According to certain investigations, p-dichlorobenzene was detected not only in houses but also in vacant lands or thickets of assorted trees 80 m apart from houses. Furthermore, p-dichlorobenzene is one of target substances for general inspection of safety of chemical substances specified by the Environmental Agency. Furthermore, it is said that p-dichlorobenzene causes liver troubles, lung granulomata, cataract and dermatitis.

In addition, p-dichlorobenzene as the moth-proofing agent is defective in that since p-dichlorobenzene contains chlorine atoms in the molecule, metallic decoration for clothes such as gold and silver threads (composed of brass, aluminum and the like) and spangles are often blackened. In order to obviate this disadvantage, naphthalene or camphor has been used. However, since the sublimation speed of naphthalene or camphor is low, naphthalene or camphor is not suitable for a preservation box which is often opened and closed. Also naphthalene is an aromatic compound, and the toxicity and residual property are comparable to those of p-dichlorobenzene. Moreover, naphthalene has a peculiar odor stronger than that of p-dichlorobenzene.

Conventional use of an insect-proofing agent is not limited to prevention of damages of clothes by moths or insects but it is required to use an insect-proofing agent in other fields. Namely, when people remain outdoors, for example, at a picnic, hiking, garden party or an athletic meeting, or the like, thus can come into contact with ants, ground beetles, shield bugs and other insects and it is often experienced that unpleasant feeling are given. Moreover, in the fields or in houses, people may be stung by ants or foods may be damaged by gathering moths or insects. An insect-proofing agent effective for preventing such damage has hardly been developed. For example, an immediate effect insecticide often used at home shows a temporary controlling action but since the insecticide is promptly volatilized off, the controlling action is not durable. Moreover, it is not the insecticidal action but the insect-proofing action that is required. Namely, it is sufficient that insects or moths are expelled, and insects or moths need not be killed. In case of a delayed effect insecticide, the action is not immediately obtained, and the residual property is ordinarily strong and environmental contamination is caused. A repellent to be applied to the human skin is insufficiently small in the effect-extending region. Moreover, these conventional agents are ordinarily oil-soluble and they are used in the form of preparations which are more or less combustible. Accordingly, use of these agents near a fire, such as an open-air fire, or a portable cooking stove, is very dangerous.

SUMMARY OF THE INVENTION

It is therefore a primary object of the present invention to provide an insect-proofing agent in which the above-mentioned defects of the conventional moth-proofing agents are eliminated.

Another object of the present invention is to provide an insect-proofing agent, especially an insect-proofing agent for clothing, which has a high insect-proofing action, no irritating odor and no toxicity to human bodies and which does not discolor metallic substances such as silver or gold yarns or spangles used for decoration of clothes.

Still another object of the present invention is to provide an insect-proofing agent which has an excellent sublimability and which can be easily applied in the form a solid, an aqueous solution, an organic solvent solution or other preparation.

A further object of the present invention is to provide an insect-proofing method in which an excellent immediate effect and an excellent durability of the insect-proofing action can be attained.

In accordance with one aspect of the present invention, there is provided an insect-proofing agent comprising 1,3,5-trioxane (hereinafter referred to as "trioxane") as an active ingredient.

In accordance with another aspect of the present invention, there is provided an insect-proofing method using 1,3,5-trioxane.

DETAILED DESCRIPTION OF THE PREFERRED EMBODIMENTS

Chemical Structure and Characteristics of Trioxane

Trioxane is a chemical substance represented by the chemical formula $(CH_2O)_3$ and having a melting point of 64° C. and is a sublimable solid which is very stable at normal temperature in air.

Trioxane is a cyclic trimer of formaldehyde, but the hydrolyzability is very low and formaldehyde is not easily released in the normal state. In this point, trioxane is distinguishable over other formaldehyde derivatives such as formalin (an aqueous solution of formaldehyde composed mainly of formaldehyde hydrate) and is not a substance deemed chemically and and paraformaldehyde (a mixture of linear polyoxymethylene glycols) physiologically equivalent to formaldehyde.

In fact, trioxane has a pleasant smell resembling that of chloroform and does not possess an irritating property possessed by formaldehyde. Trioxane has extremely low acute toxicity. The $LD_{50}$ of trioxane oral administration to rats is 8,500 mg/kg, while $LD_{50}$ of 37% by weight formalin by oral administration to rats is 800 mg/kg. From these facts, trioxane is a physiologically safe substance which is quite different from formaldehyde. The fact that trioxane has no mutagenicity has already been proved with respect to mice, rats, small fruit flies (drosophila) and salmonellae. Furthermore, trioxane has no narcotic action. Accordingly, trioxane is safer than the conventional moth-proofing agents such as p-dichlorobenzene and naphthalene. Therefore, trioxane is very low in the residual property, and hence, the environment-contaminating property is very low.

Trioxane is clearly distinguishable over the conventional moth-proofing agents in the following points.

Each of p-dichlorobenzene, naphthalene and camphor gemerates sooty black flames at combustion. Especially, burning p-dichlorobenzene generates a chlorine type poisonous gas because it contains chlorine atoms. Each of these three substances is oil-soluble but is hardly soluble or is insoluble in water.

The solubility of trioxane in saturated hydrocarbons is poor but it is highly soluble in other various organic solvents and it is also soluble in water. However, trioxane has no deliquescent property. Trioxane is further different from other moth-proofing agent in that trioxane generates a soot-free blue flame at combustion.

The insecticidal force of trioxane is weaker than that of p-dichlorobenzene but trioxane has a sufficient repellency to insects and thus trioxane is satisfactory as an insect-proofing agent. The present invention provides a safe insect-proofing agent by sufficiently utilizing these excellent characteristic properties of trioxane.

Insect-proofing Agent

The insect-proofing (including mothproofing—same hereinafter) agent comprises trioxane as an active ingredient. Trioxane having a purity as high as possible is preferably used. Trioxane having a high purity has a weak pleasant smell resembling that of chloroform.

In order to utilize this pleasant smell and keep the storage stability of trioxane, it is preferred that the content of formic acid as an impurity in trioxane be lower than 20 ppm, especially lower than 10 ppm. Furthermore, it is preferred that the content of formaldehyde be lower than 50 ppm, especially lower than 20 ppm. Trioxane sometimes contains polyoxymethylene glycol dimethyl ether as an impurity, but these compounds have no substantial influences on the smell, the storage stability, the insect-proofing action and other properties.

At least one stabilizer can be added to increase the storage stability. Any of stabilizers customarily used for trioxane can be used in the present invention. Substances having an antioxidant action or a polymerization-inhibiting action can be used as the stabilizer. For example, there can be mentioned sterically hindered phenols, disulfides, amines, thiocarbamoyl compounds and organic trivalent phosphorous compounds. The amount added of the stabilizer is determined according to the kind of the stabilizer and other conditions, and the amount added of the stabilizer is generally about 1 to about 1000 ppm.

The kind of the sterically hindered phenol is not particularly critical. A sterically hindered phenol having a relatively low molecular weight, such as 2,6-di-tert-butyl-p-cresol, can be used, but in view of the application state of the insect-proofing agent, a stabilizer having a low volatility is preferably used. Among sterically hindered phenols, pentaerythritoltetrakis[3-(3,5-di-tert-butyl-4-hydroxyphenyl)propionate] 1,6-hexandediol-bis[3-(3,5-di-tert-butyl-4-hydroxyphenyl)propionate], and triethyleneglycol-bis[3-(3-tert-butyl-4-hydroxy-5-methylphenyl)propionate] are especially preferred. Among amines, ethanolamines, especially high-boiling-point amines such as triethanolamine, are preferred.

A small amount of a flavoring agent may be added to the insect-proofing agent, if desired. However, trioxane per se has a pleasant smell, and therefore, a flavoring agent need not be particularly added. A chemical having a stronger insect-proofing or insecticidal effect than trioxane can be added, but a sufficient insect-proofing effect can be attained by using trioxane alone as the active ingredient.

Various preparations can be adopted when trioxane or a trioxane-containing composition is applied as the insect-proofing agent. For example, the insect-proofing agent can be used in the form of a solid preparation, an aqueous solution preparation or an organic solvent solution preparation.

More specifically, in accordance with one preferred embodiment of the present invention, there is provided a sublimable solid insect-proofing agent for clothes, which comprises trioxane as the active ingredient (hereinafter referred to as "solid insect-proofing agent"). Namely, trioxane per se is moldable into a solid preparation such as a pellet or a tablet, and this insect-proofing agent sublimes and shows an insect-proofing action. It is preferred that trioxane be contained in an amount of at least 99% by weight in the solid insect-proofing agent.

Since the sublimation speed of trioxane per se is high, the solid insect-proofing agent has a sufficient immediate effect and the range of the adjustment of the sublimation speed in the application state is broad. According to a method in which the solid insect-proofing agent is packed with a film member and a part of the film member is cut and removed at the time of application, sublimation is controlled and the life can be prolonged. A physicochemically stable film member is preferred, but ordinarily; the stability possessed by polyethylene, polypropylene, cellophane or poly(vinylidene chloride) is sufficient. Polyethylene and polypropylene are preferred as the film member. The sublimation speed can be adjusted by using a gas-permeable film member such as a porous film or paper or non woven fabric.

As regards the packaging form, a disk-shaped pellet can be packaged in a square form as in case of a p-dichlorobenzene preparation. If a columnar pellet is packaged in such a manner that the side face of the column is tightly covered and a space having a gradually reduced sectional area from the bottom face, that is, a conical or frustoconical space, is formed on at least one side of the bottom face of the column, the sublimation speed can be appropriately adjusted by cutting and removing the packaging material at an appropriate part of this space.

Trioxane can be used in the form of a powder, a granule or a molded body for the solid insect-proofing agent. For example, trioxane can be molded into a pellet by compression molding of powdery or granular trioxane or by cast molding or extrusion molding of molten trioxane The amount of one pack of the solid insect-proofing agent is not particularly critical, but the amount of the solid insect-proofing agent is 0.5 to 10 g, preferably 1 to 5 g, per tablet.

The insect-proofing agent of the present invention shows an insect-proofing action to not only harmful insects and moths to clothes but also other insects such as cockroaches, ants and moths. When the insect-proofing agent is used for clothes, the solid insect-proofing agent is opened in a cloth-containing portion of a clothing box or a drawer of a cloth cabinet so that trioxane is sublimated in the cloth-containing atmosphere.

The insect-proofing agent does not blacken gold and silver yarns and spangles of cloth decoration and an irritating smell as possessed by p-dichlorobenzene or naphthalene is not left in clothes at all.

The solid insect-proofing agent can be used as a fuel. In this case, the solid insect-proofing agent is packed in a can, and when the insect-proofing effect is desired, a small opening is formed, but if the solid insect-proofing agent is used as a fuel, a large opening is formed and the solid insect-proofing agent is ignited.

In accordance with another aspect of the present invention, there is provided a liquid insect-proofing agent containing trioxane in the form of an aqueous solution (hereinafter referred to as "aqueous liquid insect-proofing agent").

In this aqueous liquid insect-proofing agent of the present invention, a higher concentration of trioxane is preferable for increasing the insect-proofing action, but in order to prevent precipitation of a crystal trioxane in the application state, it is preferred that the upper limit of the trioxane concentration be 15% by weight, especially 11% by weight. If the trioxane concentration is too low, the effect is weak and the amount used of the aqueous liquid insect-proofing agent should be increased. Accordingly, it is preferred that the lower limit of the trioxane concentration by 5% by weight, especially 8% by weight.

The process for preparing the aqueous solution of trioxane is not particularly critical. For example, a melt or solid of trioxane is mixed with water at a predetermined ratio to form a solution.

Highly purified water need not be particularly used as the starting water. City water customarily used as drinking water is sufficiently used. More purified water such as distilled water or deionized water can also be used.

The so-prepared aqueous solution of trioxane can be preserved for several months to several years. In order to enhance the storage stability, trioxane having a purity as high as possible is preferably used as the starting trioxane. Moreover, a stabilizer as mentioned above is effectively used. In the case where the stabilizer is hardly soluble in water, dissolution can be facilitated by means of homogeneously incorporating the stabilizer in trioxane in advance.

Trioxane is stable in a neutral or alkaline aqueous solution, but trioxane is hydrolyzed in a highly acidic aqueous solution. In view of the safety during use, it is preferred that the hydrogen ion concentration of the aqueous liquid insect-proofing agent of the present invention be such that the pH value is 4 to 10, preferably 6 to 8. This hydrogen ion concentration can be attained without any particular pH adjustment if the above-mentioned starting materials are used. The pH value is adjusted according to a suitable method, if necessary. For example, if the pH value is within the acidic region, a suitable amount of an amine as the stabilizer may be added.

The aqueous liquid insect-proofing agent of the present invention can be scattered by a hand spray or a suitable aerosol-applying method. The amount used of the aqueous liquid insect-proofing agent is changed according to the application environment and is not simply defined. For example, if the aqueous liquid insect-proofing agent of the present invention is scattered at a rate of 0.02 to 0.1 ml/cm$^2$ on the ground in the shade to form an insect-proofing zone having a width of about 10 cm, the insect-proofing action is ordinarily maintained for about 0.5 to about 2 hours. If absorbent cotton or the like is impregnated with the aqueous liquid insect-proofing agent, and if the aqueous liquid insect-proofing agent is used in the dark and cold place where there is no substantial wind, the insect-proofing action can be maintained for a long time.

In accordance with still another embodiment of the present invention, there is provided a liquid insect-proofing agent containing trioxane in the form of an organic solvent solution (hereinafter referred to as "organic liquid insect-proofing agent").

Any of organic solvents capable of dissolving trioxane stably therein can be used without any limitation. Ordinarily, a neutral organic solvent is preferably used because it has no irritating odor or no unpleasant odor. By the neutral solvent is meant a solvent which does not contain an acidic group such as a carboxyl group or a basic group such as a basic nitrogen atom. For example, an aliphatic or aromatic hydrocarbon and a halogenated hydrocarbon are included in the category of the neutral organic solvent.

An oxygen-containing organic solvent is preferred because the trioxane-dissolving property is high, and an aliphatic organic solvent is preferred because the toxicity and environment-contaminating property are low.

A neutral oxygen-containing aliphatic organic solvent is most preferred. By the neutral oxygen-containing aliphatic organic solvent is meant an aliphatic organic solvent which is not acidic or alkaline and contains at least one oxygen atom in the molecule. As typical instances, there can be mentioned alcohols, ethers, ketones and esters.

The neutral oxygen-containing aliphatic organic solvent has a high trioxane-dissolving property and the storage stability of the solution is high. Moreover, the neutral oxygen-containing aliphatic organic solvent does not possess an irritating odor or unpleasant odor and is low in the toxicity and environment-contaminating property.

A neutral oxygen-containing aliphatic organic solvent having a boiling point lower than that of trioxane is especially preferred because a solution of trioxane in this solvent has an immediate effect as the insect-proofing agent and the residual smell is very small. As preferred examples of the solvent, there can be mentioned alcohols such as methanol, ethanol, 1-propanol and 2-propanol, ethers such as diethyl ether, dipropyl ether and diisopropyl ether, ketones such as acetone and ethyl methyl ketone, and esters such as methyl acetate, ethyl acetate and isopropyl acetate. Of these solvents, ethanol, 2-propanol, diethyl ether, diisopropyl ether, acetone and ethyl acetate are especially preferred because they have no unpleasant odor and a high safety to human bodies.

A suitable solvent is selected according to the intended use of the organic liquid insect-proofing agent. For example, ethers have a very small residual smell and have a high immediate effect. Since ketones and esters have a high trioxane-dissolving property, solutions having a high trioxane concentration can be formed. Ethanol has an especially high safety to human bodies.

In the organic liquid insect-proofing agent of the present invention, the trioxane concentration differs according to the kind of the solvent, but it is generally preferred that the trioxane concentration be about 10 to about 50% by weight. As the trioxane concentration is low, the immediate property is increased, while, as the trioxane concentration is high, the durability is increased.

The process for preparing the organic trioxane solution is not particularly critical. For example, a melt or solid of trioxane is mixed with the organic solvent at a predetermined ratio to form an organic trioxane solution. As in case of the aqueous solution, a stabilizer may be added to the solution.

The organic liquid insect-proofing agent is used in the state where the organic liquid insect-proofing agent is charged in a suitable volatilizing vessel or where cotton or paper is impregnated with the organic liquid insect-proofing agent. When an immediate effect is desired, the organic liquid insect-proofing agent may be scattered or sprayed according to a suitable spraying method.

The amount used of the organic liquid insect-proofing agent is changed according to such factors as the intended use and the application environment. For example, when the organic liquid insect-proofing agent is used for storing clothes, the amount of liquid insect-proofing agent is about 0.1 to about 2.0 g as trioxane per liter of the volume of the space in a cloth-storing vessel. This amount of trioxane is almost equal to the amount used in case of the solid insect-proofing agent.

The solvent used in the organic liquid insect-proofing agent easily volatilizes and promptly stops the action of a harmful insect or moth by the narcotic influence thereof. Then, trioxane gradually volatilizes and continues to exert the insect-proofing action.

The insect-proofing agent of the present invention is not limited to the foregoing embodiments. For example, a lubricant such as a higher fatty acid salt or a binder such as polyvinyl alcohol may be added to a solid or powdery preparation of the solid insect-proofing agent of the present invention.

Of course, the insect-proofing agent of the present invention may be used in the form of an oil-in-water or water-in-oil emulsion obtained by using a suitable surface active agent.

Moreover, the insect-proofing agent of the present invention can be used as a fumigation insect-proofing agent.

The insect-proofing agent and insect-proofing method of the present invention have the following effects.

The insect-proofing agents, in common, have a large insect-proofing action and show a pleasant smell without an irritating odor or unpleasant odor, and they are non-toxic to human bodies, do not contaminate the environment and are suitably used for clothes. Moreover, they do not discolor the metallic decorations of clothes such as gold yarns, silver yarns or spangles.

The solid insect-proofing agent of the present invention can also be used as a fuel, and the aqueous liquid insect-proofing agent of the present invention has no inflammability and can be used safely.

The organic liquid insect-proofing agent can be formed into an immediate effect type and a durable effect type.

The present invention will now be described in detail with reference to the following examples that by no means limit the scope of the invention.

EXAMPLE 1

Granular trioxane having a purity higher than 99.9% by weight and containing 6 ppm of formic acid and 10 ppm of formaldehyde was compression-molded into an insect-proofing agent in the form of a white disk-shaped pellet having a diameter of 20 mm and a thickness of 5 mm. This solid insect-proofing agent had a pleasant smell of trioxane.

A cockroach having a high escaping property was selected as the experimental insect. Namely, one adult Japanese cockroach was placed in a glass bottle having an inner diameter of 6 cm and a volume of 150 ml and one piece of fried noodle having a length of 2 cm was given as a bait to the cockroach. Since the insect ate up the bait completely, another bait was given. During the eating action, one piece of the above-mentioned solid insect-proofing agent was quietly placed at a point apart from the insect. Within 1 minute, the insect escaped from the bottom of the bottle and arrived at an insect cage through a polyethylene tube which was connecting between the bottle and the insect cage. The insect was returned to the original bottle without damaging the insect body and the bottle was covered with a metal lid and allowed to stand in the dark place. The lid had five holes having a diameter of 2 mm as vent holes. The subsequent progress was as follows. After 15 minutes:

The insect was present on the back surface of the lid in the top portion of the bottle and seemed to evade trioxane.

After 1 hour and 15 minutes:

The insect fell on the bottom of the bottle and struggled with the belly above. The insect was picked up with a pincette and restored to the normal posture.

After 3 hours:

The insect hardly moved and was dying.

After 24 hours:

The insect was dead.

EXAMPLE 2

Granular trioxane having a particle size of 2 to 5 mm and a trioxane content higher than 99.2% by weight and containing 18 ppm of formic acid, 40 ppm of formaldehyde as impurities, and 300 ppm of triphenylphosphine as the stabilizer was used as a sample of the solid insect-proofing agent. The sample had no unpleasant odor.

Ants having a high gathering property were selected as experimental insects. In each of six test tubes having a diameter of 24 mm and a length of 200 mm, absorbent cotton impregnated with an aqueous solution containing 10% by weight of granulated sugar was packed in the bottom portion. The test tubes were horizontally placed on the ground in the shade so that the months were directed to the north. Brown ants (*Laslus niger*) were active on the ground where the test tubes were placed. These test tubes were designated as tubes A through F from the east side. The distance between the tubes A and B and the distance between the tubes E and F were 3 cm respectively, and the distance between the tubes B and C and the distance between the tubes D and E were 6 cm respectively. The distance between the tubes C and D was 9 cm. The test tubes B, D and E were set with 0.2 g, 0.4 g and 0.5 g of the sample, respectively, and in each of these test tubes, the sample was placed in the inside 2 cm apart from the mouth. After the lapse of 1 hour and 30 minutes, the test tubes were observed. Many ants gathered in rows in the test tubes A, C and F in which trioxane was not set. No ant was present in the test tubes D and E charged with trioxane. Two ants were found in the test tube B in which the amount of set trioxane was small, but they did not form a row. These two ants did not touch the absorbent cotton but loitered in the intermediate portion of the test tube. It seemed that the ants could not escape from the interior of the test tube.

EXAMPLE 3

Granular trioxane having a trioxane content higher than 99.5% by weight and containing 8 ppm of formic acid, 15 ppm of formaldehyde, and 100 ppm of pentaerythritol-tetrakis 3-[3,5-di-tert-butyl-4-hydroxyphenyl)propionate] and 80 ppm of an ethanolamine mixture (comprising 2% by weight of monoethanolamine, 8% by weight of diethanolamine and 90% by weight of triethanolamine) as the stabilizers was compression-molded to obtain a solid insect-proofing agent in the form of a white disk-shaped pellet having a diameter of 20 mm and a thickness of 5 mm.

Six brown ants (*Lasius niger*) having a body length of about 3 mm were set free in a glass bottle having a volume of 200 ml, and a small piece of absorbent cotton impregnated with an aqueous solution containing 5% by weight of granulated sugar as a bait was put into the bottle. Then, the above-mentioned solid insect-proofing agent was placed in the glass bottle so that it did not touch the absorbent cotton. The mouth of the bottle was covered with a cotton fabric, and the fabric was secured by a rubber band to form an air-permeable lid. The subsequent progress was as follows. Within 10 minutes:

All of the six ants were apart from the absorbent cotton and arrived at the upper part, and the ants held fast to the back surface of the cotton fabric.
After 30 minutes:

The ants were slow in movement on the back surface of the cotton fabric.
After 1 hour:

All of the six ants fell to the bottom, and three ants moved on the absorbent cotton and the other three ants were slow in movement on the glass bottom.
After 2 hours:

All of the six ants were dying on the glass bottom.
After 18 hours:

All of the six ants were dead.

EXAMPLE 4

A tinplate can having an inner diameter of 8.2 cm and a height of 3.6 cm was charged with 200 g of a melt of trioxane having a trioxane content higher than 99.3% by weight and containing 9 ppm of formic acid, 12 ppm of formaldehyde, and 500 ppm of 2,6-di-tert-butyl-p-cresol and 100 ppm of triethanolamine as the stabilizers to obtain a canned insect-proofing agent. After the content in the can was solidified, one bottom face of the can was opened along about ¼ of the circumference by a can opener and this opened can was used as the insect-proofing agent.

Then, the partially opened bottom face of the can was completely opened, and the opened can was placed below a stainless steel beaker having a diameter of 14 cm, which was arranged on a tripod, so that the distance between the bottom face of the beaker and the opened bottom face of the can was 2 cm. The beaker was charged with 500 g of water maintained at 25° C. The beaker was lidded with a watch glass and the canned insect-proofing agent in the can was ignited by a match. The canned insect-proofing agent was easily fired and was burnt while generating a soot-free blue flame. No bad odor was generated during combustion. After 14 minutes from ignition, water was boiled. After boiling was continued for 16 minutes, a steel lid prepared in advance was placed on the can to put out the fire. The weight loss of trioxane after the combustion was 66 g and the decrease of water in the beaker was 64 g. No soot adhered to the bottom face of the beaker.

EXAMPLE 5

A melt of trioxane having a trioxane content higher than 99.8% by weight and containing 7 ppm of formic acid, 9 ppm of formaldehyde, and 80 ppm of triethyleneglycol-bis [3-(3-tert-butyl-4-hydroxy-5-methylphenyl)propionate] and 20 ppm of triethanolamine as the stabilizers was cast in a mold and solidified to form two white columnar pellets of a solid insect-proofing agent having a bottom face diameter of 10 mm and a height of 30 mm. One pellet was filled in a polyethylene film tube (film thickness=0.04 mm) having the same diameter and the side face was covered. Then the open end of the tube was fused under heating and drawing and press-bonded to seal the pellet in the conical form.

Each of two beakers having a volume of 500 ml was charged with a square aluminum foil having a side of 10 cm and a thickness of 15 μm. The covered pellet which was opened by cutting the top part of the conical package was placed in one beaker and the uncovered pellet was placed in the other beaker. The beakers were sealed with a polyethylene film and allowed to stand at room temperature for 3 months in summer. In each beaker, the surface of the aluminum foil, inclusive of the surface brought into contact with the uncovered pellet, was not changed at all.

EXAMPLES 6 AND 7 AND COMPARATIVE EXAMPLES 1 to 6

Granular trioxane having a trioxane content higher than 99.9% by weight and containing 5 ppm of formic acid, 8 ppm of formaldehyde, and 50 ppm of 1,6-hexanediol-bis [3-(3,5-di-tert-butyl-4-hydroxyphenyl)propionate] and 8 ppm of triethanolamine as the stabilizers was compression-molded to prepare a solid insect-proofing agent in the form a white disk-shaped pellet having a diameter of 20 mm and a thickness of 5 mm. The solid insect-proofing agent was subjected to the test for controlling harmful insects to clothes.

A glass bottle having a volume of 500 ml was charged with 10 harmful insects and one square wool fabric piece having a side of 3 cm, and one pellet of the solid insect-proofing agent was placed apart from the wool fabric piece. The bottle was tightly plugged and was allowed to stand in the dark place at a temperature of 24° to 26° C.

For comparison, commercially available moth-proofing agents, p-dichlorobenzene and naphthalene (each was in the form of a flat disk-shaped pellet having a diameter of 21 mm), were similarly tested, and the test was carried out without using any moth-proofing agent. The wool fabric pieces were observed with the naked eye, and the eating damage degree was evaluated according to the following 4-rank rating.

A: no eating damage
B: eating damage was only a trace
C: intermediate between ranks B and D
D: large eating damage (damage in absence of insect-proofing agent)

The results of the tests conducted on larvae of case making clothes moths having a body length of about 6 mm as the harmful insects (Example 6 and Comparative Examples 1 to 3) are shown in Table 1, and the results of the test conducted on larvae of varied carpet beetles having a body length of about 4 mm as harmful insects (Example 7 and Comparative Examples 4 to 6) are shown in Table 2.

TABLE 1

| | Example 6 | Comparative Example 1 | Comparative Example 2 | Comparative Example 3 |
|---|---|---|---|---|
| Insect-proofing agent | present invention | p-dichlorobenzene | naphthalene | not added |
| Number of dead insects after 6 hours | 2 | 5 | 0 | 0 |
| Number of dead insects after 24 hours | 10 | 10 | 2 | 0 |
| Eating damage degree after 24 hours | A | A | B | D |

TABLE 2

| | Example 7 | Comparative Example 4 | Comparative Example 5 | Comparative Example 6 |
|---|---|---|---|---|
| Insect-proofing agent | present invention | p-dichlorobenzene | naphthalene | not added |
| Number of dead insects after 6 hours | 1 | 3 | 0 | 0 |
| Number of dead insects after 24 hours | 10 | 9 | 0 | 0 |
| Eating damage degree after 24 hours | A | A | C | D |

EXAMPLE 8

Granular trioxane containing 15 ppm of formic acid and 28 ppm of formaldehyde was dissolved in deionized water (deionized city water with an ion-exchange resin) to prepare an aqueous solution having a trioxane concentration of 6% by weight and a pH value of 5.8. This aqueous solution was used as an aqueous liquid insect-proofing agent.

Absorbent cotton piece impregnated with an aqueous solution containing 5% by weight of sucrose was placed at two points on the ground in the shade in a residential square. Around one absorbent cotton, piece 40 ml of the aqueous liquid insect-proofing agent was uniformly scattered in an annular zone having an average radius of about 20 cm and a width of about 10 cm with the absorbent cotton piece being as the center by using a watering pot having fine holes. After 1 hour, the two points of absorbent cotton pieces were observed. Red ants gathered in rows on the absorbent cotton piece not surrounded by the scattered aqueous liquid insect-proofing agent, and one bee deemed to be a kind of a long-legged wasp was found to fly to this absorbent cotton piece. No insect gathered on the absorbent cotton, around which the aqueous liquid insect-proofing agent has been scattered.

COMPARATIVE EXAMPLE 7

At the same time of the aqueous liquid insect-proofing agent-scattering test in Example 8, a test was carried out in the same manner as described in Example 8 except that the aqueous solution containing 10 ppm of formic acid and 10 ppm of formaldehyde (in this solution, the formic acid concentration was 11 times as high as the formic acid concentration in the aqueous liquid insect-proofing agent used in Example 8 and the formaldehyde concentration was 6 times as high as the formaldehyde concentration in the aqueous liquid insect-proofing agent used in Example 8) was used instead of the aqueous liquid insect-proofing agent used in Example 8. After 1 hours, have the absorbent cotton piece was observed. Many red ants in rows and two bees gathered on the absorbent cotton piece. It was confirmed that the solution used had no insect-proofing action.

EXAMPLE 9

Granular trioxane containing 2 ppm of formic acid, 3 ppm of formaldehyde, and 50 ppm of pentaerythritoltetrakis[3-(3,5-di-tert-butyl-4-hydroxyphenyl)propionate] and 200 ppm of triethanolamine as the stabilizers were dissolved in city water to form an aqueous solution having a trioxane concentration of 10% by weight and a pH value of 7.5 as an aqueous liquid insect-proofing agent. After 6 months' storage, the aqueous liquid insect-proofing agent was applied to rows of ants.

Many red ants intruded in a row into a reinforced concrete building from the outside. On the outside of the building, 50 ml of the aqueous liquid insect-proofing agent was scattered in the regions within about 30 cm on both the sides of the row of ants with a width of about 10 cm by using a trigger type spraying bottle. Just after scattering, the row was disturbed and the ants in the scattered region escaped from this region, and no ant intruded in the scattered region. This state was continued for at least 2 hours after scattering. On the next day, however, a row of ants was similarly formed. No ant died.

EXAMPLE 10 AND COMPARATIVE EXAMPLE 8

To a melt of trioxane containing 6 ppm of formic acid and 12 ppm of formaldehyde were added 200 ppm of 2,6-di-tert-butyl-p-cresol and 100 ppm of triethanolamine as the stabilizers, and the melt was dissolved in city water to form an aqueous solution having a trioxane concentration of 11% by weight and a pH value of 7.1 as an aqueous liquid insect-proofing agent.

The aqueous liquid insect-proofing agent was used in a house having an openable-closable floor board in a kitchen, and a rice box, an edible oil and the like were kept in a space below this floor board and cockroaches were always rampant in this space.

Two commercially available adhesive cockroach catchers were set up below the floor board. Absorbent cotton piece having a width of 2 cm and a length of 60 cm, which was impregnated with 36 ml of the above-mentioned aqueous liquid insect-proofing agent, was annularly arranged around one cockroach catcher, and absorbent cotton piece of the same size impregnated with 36 ml of city water was annularly arranged around the other cockroach catcher. After one week, the cockroach catchers were examined. No insect was caught on the catcher surrounded by the absorbent cotton piece impregnated with the aqueous liquid insect-proofing agent, but seven large and small cockroaches (having a body length of 1 to 5 cm) were caught on the other cockroach catcher.

EXAMPLES 11 through 16

Granular trioxane containing 1 ppm of formic acid and 2 ppm of formaldehyde was dissolved in various organic solvents at a predetermined concentration to prepare organic liquid insect-proofing agents.

Square absorbent cotton piece having a side of 3 cm, which was impregnated with 2 g of the organic liquid insect-proofing agent, was placed in the bottom portion of a glass bottle having a volume of 500 ml, and an insect cage of a metal net having a diameter of 3 cm, which contained 10 larvae of case making clothes moths having a body length of about 6 mm and a square wool fabric having a side of 3 cm, was secured the absorbent cotton 5 cm apart therefrom. Then, the bottle was plugged and allowed to stand in a thermostat chamber maintained at 25° C. for 4 hours. Then, the cage was taken up and the state of the larvae of case making clothes moths was checked. The obtained results are shown in Table 3. In each run, no eating damage of the wool fabric was observed.

TABLE 3

| Example No. | Solvent | Trioxane Concentration (% by weight) | Number of Killed Insects |
|---|---|---|---|
| 11 | ethanol | 15 | 10 |
| 12 | 2-propanol | 10 | 10 |
| 13 | diethyl ether | 25 | 10 |
| 14 | diisopropyl ether | 15 | 10 |
| 15 | acetone | 30 | 10 |
| 16 | ethyl acetate | 50 | 10 |

COMPARATIVE EXAMPLES 9 to 13

The tests were carried out in the same manner as described in Examples 11 through 16 except that chemicals shown in Table 4 were used in the solid state instead of the absorbent cottom piece impregnated with the organic liquid insect-proofing agent of the present invention. These tests were conducted simultaneously with the tests of Examples 11 through 16. Each of p-dichlorobenzene, naphthalene and dl-camphor was used in the form of a granular reagent. Granular trioxane used in Examples 11 through 16 for the production of the organic liquid insect-proofing agent was used as the solid trioxane. One pack of "Mothproofing Agent for Drawers" supplied by Dainippon Jochugiku (corresponding to 12.5 liters) was used as the pyrethroid type chemicals. No chemical was used in Comparative Example 13.

The obtained results are shown in Table 4. Incidentally, in every Example, the eating damage is observed.

TABLE 4

| Comparative Example No. | Chemicals | Amount | Number of Killed Insects |
|---|---|---|---|
| 9 | p-dichlorobenzene | 2 g | 2 |
| 10 | naphthalene | 2 g | 0 |
| 11 | dl-camphor | 2 g | 0 |
| 12 | pyrethroid type chemicals | corresponding to 12.5 liters | 2 |
| 13 | not added | — | 0 |

We claim:
1. A moth-proofing method which comprises applying a moth-proofing effective amount of tableted or granulated 1,3,5-trioxane having the following structural formula:

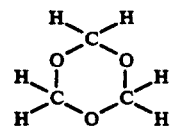

as the sole active moth-proofing agent to an area from which moths are to be excluded, said 1,3,5-trioxane containing no more than about 20 ppm of formic acid and no more than about 50 ppm of formaldehyde.

2. The method according to claim 1, wherein the tableted or granulated 1,3,5-trioxane is sublimated in a space from which moths are to be excluded.

3. The method according to claim 2, wherein the 1,3,5-trioxane is opened to said space in the form of tablet or granule.

4. The method according to claim 2, wherein the amount of the tableted or granulated 1,3,5-trioxane is from about 0.1 to about 2 grams per liter of volume of said space.

5. The method according to claim 1, wherein the tableted or granulated 1,3,5-trioxane further comprises from about 1 to 1,000 ppm of a stabilizer selected from the group consisting of sterically hindered phenols, disulfides, amines, thiocarbamoyl compounds and organic trivalent phosphorous compounds.

6. The method according to claim 1, wherein the tableted or granulated 1,3,5-trioxane comprises at least 99% by weight of the 1,3,5-trioxane having the following structural formula:

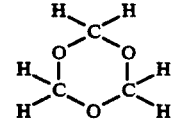

7. A method for protecting clothing from clothing-damaging moths, which comprises placing in close proximity to said clothing a sublimable moth-proofing agent package containing a moth-proofing effective amount of a sublimable tablet or granule form of 1,3,5-trioxane having the following structural formula:

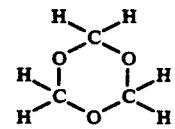

wherein said 1,3,5-trioxane is the sole active moth-proofing agent.

8. The method according to claim 7, wherein the sublimable tablet or granule form of 1,3,5-trioxane is provided with a film member packaging.

9. The method according to claim 8, wherein the film member is a film of polyethylene, polypropylene, cellophane, or poly(vinylene chloride).

* * * * *